(12) United States Patent
Kobayashi

(10) Patent No.: US 9,801,537 B2
(45) Date of Patent: Oct. 31, 2017

(54) IMAGE PROCESSING DEVICE AND METHOD, EYE FUNDUS IMAGE PROCESSING DEVICE, IMAGE PHOTOGRAPHING METHOD, AND EYE FUNDUS IMAGE PHOTOGRAPHING DEVICE AND METHOD

(71) Applicant: SONY CORPORATION, Tokyo (JP)

(72) Inventor: Seiji Kobayashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 8 days.

(21) Appl. No.: 14/908,608

(22) PCT Filed: Jul. 31, 2014

(86) PCT No.: PCT/JP2014/004018
§ 371 (c)(1),
(2) Date: Jan. 29, 2016

(87) PCT Pub. No.: WO2015/019586
PCT Pub. Date: Feb. 12, 2015

(65) Prior Publication Data
US 2016/0166142 A1   Jun. 16, 2016

(30) Foreign Application Priority Data
Aug. 7, 2013   (JP) ................................ 2013-163781

(51) Int. Cl.
*A61B 3/14*   (2006.01)
*A61B 3/00*   (2006.01)
(Continued)

(52) U.S. Cl.
CPC .............. *A61B 3/0025* (2013.01); *A61B 3/12* (2013.01); *A61B 3/14* (2013.01); *G06T 3/0018* (2013.01);
(Continued)

(58) Field of Classification Search
CPC ............ A61B 3/0025; A61B 3/12; A61B 3/14
(Continued)

(56) References Cited

U.S. PATENT DOCUMENTS 7,926,945 B2   4/2011   Dick et al.

FOREIGN PATENT DOCUMENTS

EP   2 256 688 A1   12/2010
JP   2003-10134 A   1/2003
(Continued)

OTHER PUBLICATIONS

International Search Report issued Nov. 10, 2014 in PCT/JP2014/004018.
(Continued)

*Primary Examiner* — Jack Dinh
(74) *Attorney, Agent, or Firm* — Oblon, McClelland, Maier & Neustadt, L.L.P.

(57) ABSTRACT

An eye fundus image photographing device and method that can acquire images of higher quality. The eye fundus image photographing device photographs a wide-angle eye fundus image on an appropriate exposure condition with respect to a peripheral area different from an optic disk region of an eye fundus area and detects the optic disk region from the wide-angle eye fundus image. Moreover, based on the detection result of the optic disk region, the eye fundus image photographing device photographs a narrow-angle eye fundus image which assumes an area of the optic disk region as an object, on an appropriate exposure condition with respect to the area of the optic disk region. Further, the eye fundus image photographing device generates a synthetic eye fundus image of a high dynamic range by synthesizing the wide-angle eye fundus image and the narrow-angle eye fundus image.

15 Claims, 4 Drawing Sheets

(51) Int. Cl.
    *A61B 3/12*         (2006.01)
    *G06T 5/50*        (2006.01)
    *G06T 3/00*        (2006.01)

(52) U.S. Cl.
    CPC ...... *G06T 5/50* (2013.01); *G06T 2207/10144* (2013.01); *G06T 2207/30041* (2013.01)

(58) Field of Classification Search
    USPC ................................................ 351/206, 246
    See application file for complete search history.

(56) References Cited

FOREIGN PATENT DOCUMENTS

| | | |
|---|---|---|
| JP | 2003-52639 A | 2/2003 |
| JP | 2005-270152 A | 10/2005 |
| JP | 2011-31027 A | 2/2011 |
| JP | 2011-125463 A | 6/2011 |
| JP | 2011-189202 A | 9/2011 |
| JP | 2012-213555 A | 11/2012 |
| JP | 5214538 B2 | 6/2013 |

OTHER PUBLICATIONS

T. Mertens et al., "Exposure Fusion: A Simple and Practical Alternative to High Dynamic Range Photography", Computer Graphics Forum, vol. 28, No. 1, XP055011663, Mar. 1, 2009, pp. 161-171.

IMAGE PROCESSING DEVICE AND METHOD, EYE FUNDUS IMAGE PROCESSING DEVICE, IMAGE PHOTOGRAPHING METHOD, AND EYE FUNDUS IMAGE PHOTOGRAPHING DEVICE AND METHOD

TECHNICAL FIELD

The present technology relates to an image processing device and method, an eye fundus image processing device, an image photographing method and an eye fundus image photographing device and method. Especially, the present technology relates to an image processing device and method, an eye fundus image processing device, an image photographing method and an eye fundus image photographing device and method that can acquire images of higher quality.

CROSS REFERENCE TO RELATED APPLICATIONS

This application claims priority to Japanese Priority Patent Application JP 2013-163781 filed on Aug. 7, 2013, the entire contents of which are incorporated herein by reference.

BACKGROUND ART

For example, in an eye fundus camera that photographs patient's eye fundus image in the checkup or the ophthalmologic examination, a photographing function in a high dynamic range is desired to stably acquire an eye fundus image of high quality.

In an eye fundus image assuming person's eye fundus as an object, the reflection of a light source is strong and blown-out highlights are likely to be caused in an optic disk region from which retinal nerves come out in a bundled manner, and the reflection intensity is weak and therefore blocked-up shadows are likely to be caused in a macular region corresponding to the central fovea.

To perform photographing so as not to cause the blown-out highlights in the optic disk region, the exposure setting at the time of the photographing has to be optimized and the photographer's skill is demanded. Moreover, even if photographing is performed so as not to cause the blown-out highlights in the optic disk region, the macular region and the peripheral region may be filled with black and become difficult to be diagnosed. In view of such state, a photographing function in a high dynamic range is desired for an eye fundus camera.

Therefore, as a technique to acquire an eye fundus image of a high dynamic range, there is suggested a method of defining the suitable light quantity in each region on the basis of the first photographing result (for example, see JP 2011-31027 A).

In this method, first, the light quantities of the optic disk region and the periphery are acquired by the first photographing, and, in the second photographing, photographing is performed by a suitable light quantity with respect to an area of the optic disk region which is defined by the first photographing and the area of the optic disk region is extracted from an acquired image.

Further, in the third photographing, photographing is performed by a suitable light quantity with respect to a peripheral area near the optic disk region which is defined by the first photographing, and the peripheral area is extracted from an acquired image. Moreover, the area of the optic disk region and the peripheral area which are acquired as above are synthesized to acquire one eye fundus image of a high dynamic range.

CITATION LIST

Patent Literature

PTL 1: JP 2011-31027 A

SUMMARY OF INVENTION

Technical Problem

However, in the related art described above, it is difficult to acquire an eye fundus image of high quality.

For example, in a case where an eye fundus image is photographed by a non-mydriatic camera, it is considered that miosis occurs during three times of photographing. Especially in the above-mentioned technique, since the peripheral area is photographed in the third photographing, when the miosis is caused, the image quality of the image of the peripheral area is deteriorated by the influence.

The present technology is made in view of such a situation, and it is possible to acquire an image of higher quality.

Solution to Problem

An image processing device according to a first aspect of the present technology includes: a detection unit configured to detect a narrow-angle area of a wide-angle image, wherein the wide-angle image was generated using a first exposure condition, the first exposure condition based on a first area of the wide-angle image, different from the narrow-angle area; a control unit configured to determine a second exposure condition for the narrow-angle area; and an image synthesis unit configured to generate a synthetic image by synthesizing a narrow-angle image and the wide-angle image, wherein the narrow-angle image has a narrower angle of view than the wide-angle image and was generated using the second exposure condition.

The image synthesis unit can generate the synthesis image by synthesizing a plurality of narrow-angle images that are continuously photographed and the wide-angle image.

The image synthesis unit can perform motion compensation on the plurality of narrow-angle images and synthesize the plurality of narrow-angle images acquired by the motion compensation and the wide-angle image.

The control unit can determine a pixel area in order to photograph the narrow-angle image using the pixel area and based on a detection of the narrow-angle area.

The control unit can control a light source that outputs illumination light irradiated to the narrow-angle area or a photographing unit that photographs the narrow-angle image based on the second exposure condition with respect to the narrow-angle area.

The control unit can control a light source such that the narrow-angle area is illuminated by equal light outputs from the light source when the wide-angle image is photographed and when the narrow-angle image is photographed.

The second exposure condition is set such that a pixel of the narrow-angle area in the narrow-angle image is not saturated.

According to the first aspect of the present technology, a narrow-angle area is detected from a wide-angle image, wherein the wide-angle image was generated using a first exposure condition, the first exposure condition based on a first area of the wide-angle image, different from the narrow-angle area, a second exposure condition for the narrow-angle area is determined, and a synthetic image is generated by synthesizing a narrow-angle image and a wide-angle image, wherein the narrow-angle image has a narrower angle of view than the wide-angle image and was generated for the narrow-angle area using the second exposure condition.

An eye fundus image processing device according to a second aspect of the present technology includes: a detection unit configured to detect a narrow-angle area of an eye fundus from a wide-angle image, wherein the wide-angle image was generated using a first exposure condition, the first exposure condition based on a first area of the eye fundus, different from the narrow-angle area; a control unit configured to determine a second exposure condition for the narrow-angle area of the eye fundus; and an image synthesis unit configured to generate a synthetic image by synthesizing a narrow-angle image and the wide-angle image, wherein the narrow-angle image has a narrower angle of view than the wide-angle image and was generated for the narrow-angle area of the eye fundus using the second exposure condition.

The narrow-angle area of the eye fundus can be an area of an optic disk.

According to the second aspect of the present technology, a narrow-angle area of an eye fundus is detected from a wide-angle image, wherein the wide-angle image was generated using a first exposure condition, the first exposure condition based on a first area of the eye fundus, different from the narrow-angle area, a second exposure condition is determined for the narrow-angle area of the eye fundus, and a synthetic image is generated by synthesizing a narrow-angle image and the wide-angle image, wherein the narrow-angle image has a narrower angle of view than the wide-angle image and was generated for the narrow-angle area of the eye fundus using the second exposure condition.

An image processing method according to a third aspect of the present technology includes detecting a narrow-angle area of a wide-angle image, wherein the wide-angle image was generated using a first exposure condition, the first exposure condition based on a first area of the wide-angle image, different from the narrow-angle area, determining a second exposure condition for the narrow-angle area, and generating a synthetic image by synthesizing a narrow-angle image and the wide-angle image, wherein the narrow-angle image has a narrower angle of view than the wide-angle image and was generated for the narrow-angle area using the second exposure condition.

According to the third aspect of the present technology, a narrow-angle area is detected from a wide-angle image, wherein the wide-angle image was generated using a first exposure condition, the first exposure condition based on a first area of the wide-angle image, different from the narrow-angle area, a second exposure condition is determined for the narrow-angle area, and a synthetic image is generated by synthesizing a narrow-angle image and the wide-angle image, wherein the narrow-angle image has a narrower angle of view than the wide-angle image and was generated for the narrow-angle area using the second exposure condition.

An image photographing method according to a fourth aspect of the present technology includes photographing a wide-angle image using a first exposure condition based on a first area of the wide-angle image, determining a second exposure condition for a narrow-angle area, different from the first area, based on the wide-angle image, and photographing a narrow-angle image having a narrower angle of view than the wide-angle image, based on the second exposure condition and the narrow-angle area.

In the image photographing method, it is possible to detect the narrow-angle area based on the wide-angle image and determine the second exposure condition with respect to the narrow-angle area based on a detection result of the narrow-angle area.

Photographing the narrow-angle image comprises continuously photographing a plurality of narrow-angle images.

The narrow-angle image can be photographed using a pixel area of a photographing unit, the pixel area determined based on the detection result of the narrow-angle area.

A light source can be controlled such that the narrow-angle area is illuminated by equal light outputs from the light source when photographing the wide-angle image and when photographing the narrow-angle image.

The second exposure condition can be set such that a pixel of the narrow-angle area in the narrow-angle image is not saturated.

According to the fourth aspect of the present technology, photographing is performed to photograph a wide-angle image using a first exposure condition based on a first area of the wide-angle image, a second exposure condition is determined for a narrow-angle area, different from the first area, based on the wide-angle image, and photographing is performed to photograph a narrow-angle image having a narrower angle of view than the wide-angle image, based on the second exposure condition and the narrow-angle area.

The eye fundus image photographing method according to a fifth aspect of the present technology includes photographing a wide-angle image using a first exposure condition based on a first area of the wide-angle image, determining a second exposure condition for a narrow-angle area of an eye fundus, different from the first area, based on the wide-angle image, and photographing a narrow-angle image having a narrower angle of view than the wide-angle image, based on the second exposure condition and the narrow-angle area of the eye fundus.

The narrow-angle area of the eye fundus can be an area of an optic disk.

According to the fifth aspect of the present technology, photographing is performed to photograph a wide-angle image using a first exposure condition based on a first area of the wide-angle image, a second exposure condition for a narrow-angle area of an eye fundus, different from the first area, is determined based on the wide-angle image, and photographing is performed to photograph a narrow-angle image having a narrower angle of view than the wide-angle image, based on the second exposure condition and the narrow-angle area of the eye fundus.

An eye fundus image photographing device according to a sixth aspect of the present technology includes: a photographing unit configured to photograph a wide-angle image using a first exposure condition based on a first area of an eye fundus, and photograph a narrow-angle image, having a narrower angle of view than the wide-angle image, using a second exposure condition based on a narrow-angle area of the eye fundus, a detection unit configured to detect the narrow-angle area of the eye fundus from the wide-angle image based on the wide-angle image, a control unit configured to determine the second exposure condition with respect to the narrow-angle area of the eye fundus based on the detection of the narrow-angle area of the eye fundus, and an image synthesis unit configured to generate a synthetic image by synthesizing the narrow-angle image and the wide-angle image.

According to the sixth aspect of the present technology, a wide-angle image is photographed using a first exposure condition based on a first area of an eye fundus, a narrow-angle image is photographed having a narrower angle of view than the wide-angle image using a second exposure condition based on a narrow-angle area of the eye fundus, the narrow-angle area of the eye fundus is detected from the wide-angle image based on the wide-angle image, the second exposure condition with respect to the narrow-angle area of the eye fundus is determined based on the detection of the narrow-angle area of the eye fundus, and a synthetic image is generated by synthesizing the narrow-angle image and the wide-angle image.

Advantageous Effects of Invention

According to first to sixth aspects of the present technology, it is possible to acquire an image of higher quality.

DESCRIPTION OF EMBODIMENTS

In the following, embodiments to which the present technology applies are described with reference to the drawings.

First Embodiment

<Outline of the Present Technology>
First, the outline of the present technology is described.
According to an embodiment of the present technology, by synthesizing an image of the entire eye fundus photographed under high illumination intensity and an image of the optic disk region of the eye fundus photographed under low illumination intensity, it is possible to acquire an eye fundus image of high quality with a wide dynamic range.

Figure 1:
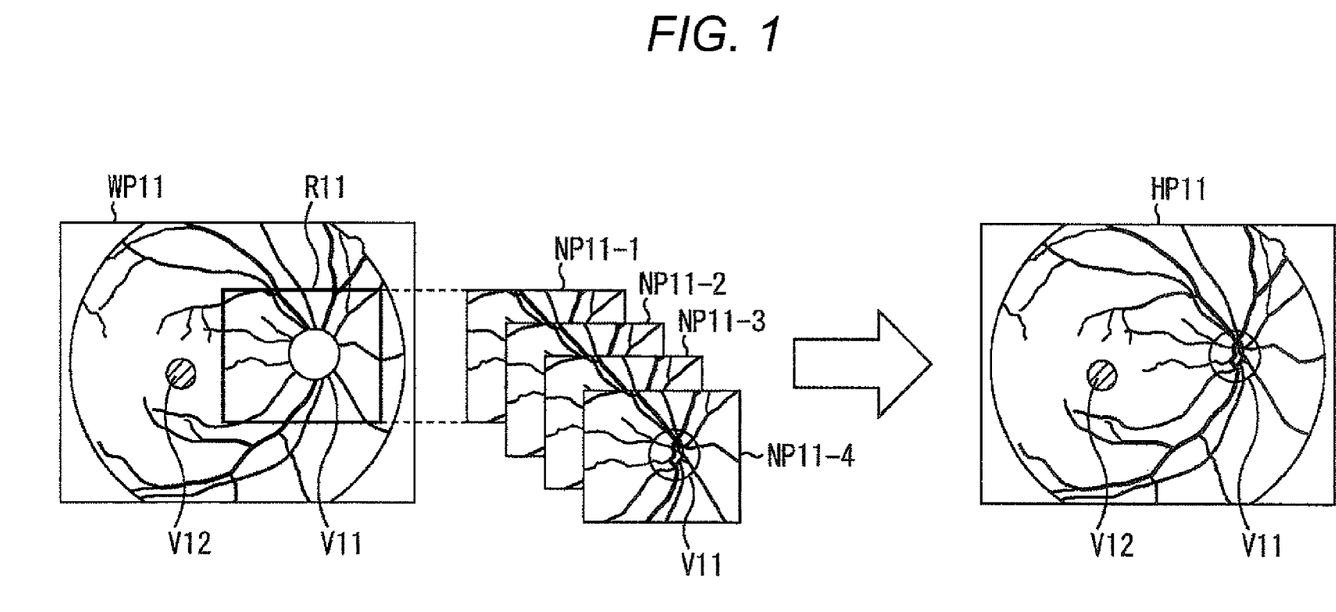
FIG. 1 is a diagram to describe the outline of the present technology.

Specifically, in an eye fundus image photographing device to which the present technology applies, for example, as the first photographing processing as illustrated in FIG. 1, an eye fundus area that is an object is photographed under high illumination intensity and wide-angle eye fundus image WP11 is acquired as a result.

Wide-angle eye fundus image WP11 is an eye fundus image photographed with a wide angle of view. In this example, wide-angle eye fundus image WP11 includes optic disk region V11 and macular region V12. Generally, it is known that blown-out highlights are likely to occur in optic disk region V11 and blocked-up shadows are likely to occur in macular region V12.

In the first photographing processing, the photographing is performed on exposure conditions on which blown-out highlights and blocked-up shadows are not caused in other areas than optic disk region V11 such as macular region V12, that is, in the peripheral area of optic disk region V11 (which may also be referred to as "peripheral area" below). That is, the photographing is performed on adaptive exposure conditions with respect to the peripheral area. By this means, it is possible to acquire wide-angle eye fundus image WP11 in which the signal to noise ratio (SN ratio) of the peripheral area is high and it is possible to sufficiently observe the peripheral area.

Moreover, when wide-angle eye fundus image WP11 is acquired, the area of optic disk region V11 is detected from wide-angle eye fundus image WP11 in the eye fundus image photographing device, and, based on the detection result, exposure conditions in the second photographing processing are decided.

For example, since wide-angle eye fundus image WP11 is photographed on the appropriate exposure conditions with respect to the peripheral area, blown-out highlights are supposed to occur in the area of optic disk region V11. Therefore, by detecting a high brightness area on wide-angle eye fundus image WP11 in the eye fundus image photographing device, the area of optic disk region V11 is detected.

Moreover, the exposure conditions in the second photographing processing are set to appropriate exposure conditions with respect to the area of optic disk region V11, on which blown-out highlights and blocked-up shadows are not caused in optic disk region V11. That is, exposure conditions on which it is possible to sufficiently observe the area of optic disk region V11 are set.

When the exposure conditions are decided, an area including optic disk region V11 is photographed under low illumination intensity as the second photographing processing. In this example, an eye fundus area corresponding to area R11 on wide-angle eye fundus image WP11 is continuously photographed at a high frame rate on the decided exposure conditions.

By this means, four narrow-angle eye fundus images NP11-1 to NP11-4 are acquired. Here, in the following, in a case where narrow-angle eye fundus images NP11-1 to NP11-4 do not have to be especially distinguished, they may be simply referred to as "narrow-angle eye fundus image NP11".

Narrow-angle eye fundus image NP11 is an image with a narrower angle of view than wide-angle eye fundus image WP11. For example, all effective pixels of an image sensor are used in the photographing of wide-angle eye fundus image WP11, and partial pixels of all effective pixels of the image sensor are used in the photographing of narrow-angle eye fundus image NP11. Thus, when photographing is performed using only part of the effective pixel area by limiting the photographing range to an area near the optic disk region in the eye fundus area in this way, the data amount to be processed decreases and therefore it is possible to perform the photographing at a high frame rate.

When wide-angle eye fundus image WP11 and narrow-angle eye fundus image NP11 are acquired in this way, the eye fundus image photographing device synthesizes acquired wide-angle eye fundus image WP11 and narrow-angle eye fundus image NP11 to generate one synthetic eye fundus image HP11. This synthetic eye fundus image HP11 is an image with the same angle of view as wide-angle eye fundus image WP11, which is a high dynamic range image acquired by synthesizing narrow-angle eye fundus image NP11 on wide-angle eye fundus image WP11.

In synthetic eye fundus image HP11, it is possible to sufficiently observe both areas of the area of optic disk region V11 and a peripheral area including macular region V12. That is, neither blown-out highlights nor blocked-up shadows are caused in each area of synthetic eye fundus image HP11.

As described above, according to an embodiment of the present technology, by photographing wide-angle eye fundus image WP11 in the first photographing processing, photographing narrow-angle eye fundus image NP11 in the second photographing processing and synthesizing those images, it is possible to acquire synthetic eye fundus image HP11 by two times of photographing. Therefore, as compared with a case where photographing is performed three times or more like the related art, it is possible to suppress deterioration of image quality due to miosis and acquire an eye fundus image of higher quality.

Especially, vignetting is caused in the edge of the visual field when the miosis occurs at the time of non-mydriatic photographing, and the deterioration of the image quality is caused in an area of the image edge. However, in the second photographing processing by the eye fundus image photographing device to which the present technology applies, since a narrow-angle eye fundus image with a narrower angle of view is photographed using the optic disk region positioned near the visual field center as a main object, it is possible to further suppress the image deterioration due to the miosis.

<Configuration Example of Eye Fundus Image Photographing Device>

Next, the eye fundus image photographing device to which the present technology applies is described more specifically.

Figure 2:
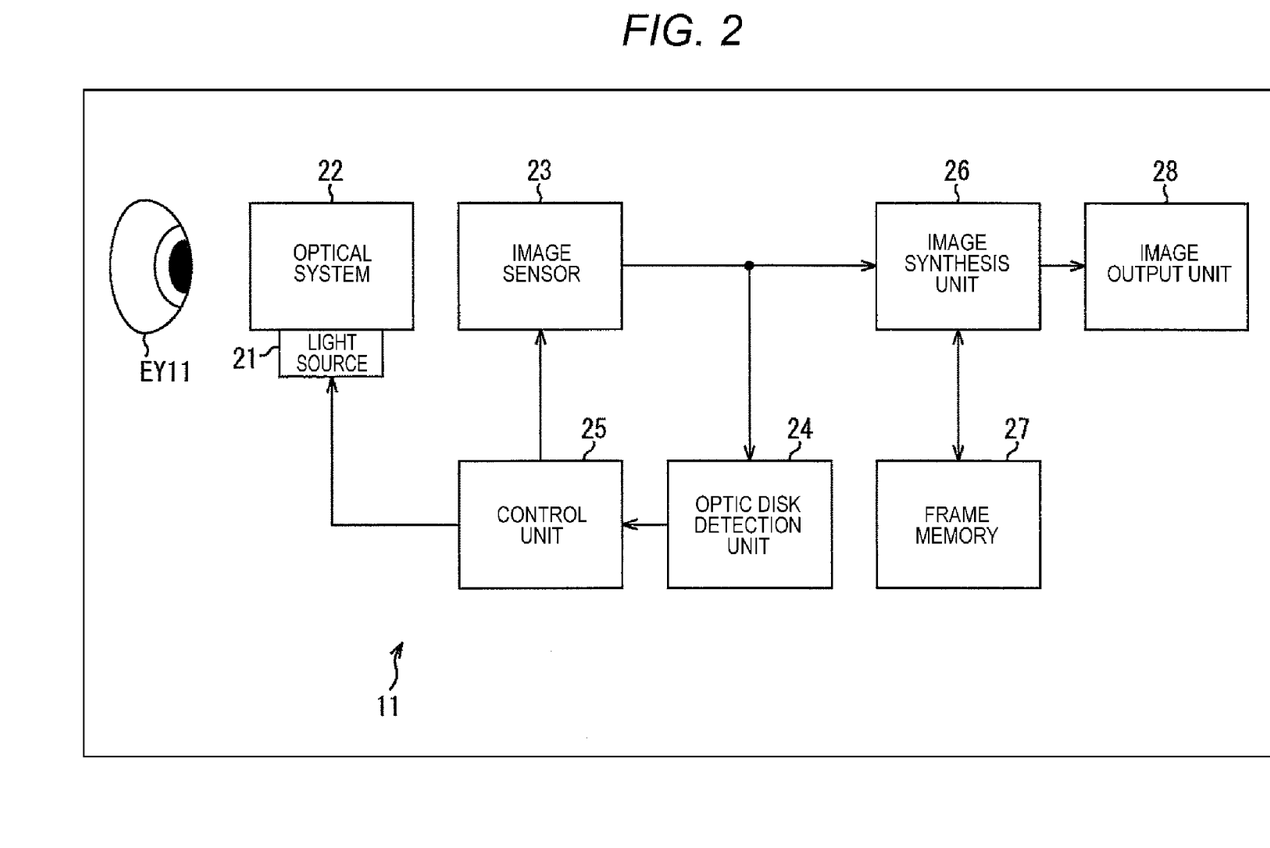
FIG. 2 is a diagram illustrating a configuration example of an eye fundus image photographing device.

FIG. 2 is a diagram illustrating a configuration example of the eye fundus image photographing device to which the present technology applies.

An eye fundus image photographing device 11 includes a light source 21, an optical system 22, an image sensor 23, an optic disk detection unit 24, a control unit 25, an image synthesis unit 26, a frame memory 27 and an image output unit 28.

The light source 21 emits illumination light that illuminates the eye fundus of eye EY11 of a person who is the photographing target, according to the control of the control unit 25. The illumination light emitted from the light source 21 is irradiated to the eye fundus of eye EY11 through the optical system 22.

The optical system 22 includes one or multiple lenses or half mirrors or the like, irradiates the illumination light entered from the light source 21 to the eye fundus of eye EY11, focuses light entered from the eye fundus of eye EY11 and leads it to the light receiving surface of the image sensor 23.

For example, the image sensor 23 includes, for example, a complementary metal oxide semiconductor (CMOS) image sensor or the like, and, by receiving the light entered from the optical system 22 and performing photoelectric conversion according to the control of the control unit 25, photographs a wide-angle eye fundus image or narrow-angle eye fundus image as an image of the eye fundus. The image sensor 23 supplies electrical signals acquired by the photoelectric conversion to the optic disk detection unit 24 and the image synthesis unit 26 as an image signal of the photographed image.

The optic disk detection unit 24 detects an optic disk region from the wide-angle eye fundus image supplied from the image sensor 23 and supplies the detection result and the wide-angle eye fundus image to the control unit 25. The control unit 25 decides exposure conditions with respect to the eye fundus that is an object and decides the photographing range of the narrow-angle eye fundus image, on the basis of the detection result and wide-angle eye fundus image supplied from the optic disk detection unit 24. Moreover, the control unit 25 controls the light source 21 and the image sensor 23 according to the decided exposure conditions and photographing range of the narrow-angle eye fundus image.

The image synthesis unit 26 arbitrarily supplies the wide-angle eye fundus image and narrow-angle eye fundus image supplied from the image sensor 23 to the frame memory 27 to record them, synthesizes the wide-angle eye fundus image and the narrow-angle eye fundus image to generate a synthetic eye fundus image, and supplies the acquired synthetic eye fundus image to the image output unit 28. The frame memory 27 temporarily records the images supplied from the image synthesis unit 26 and supplies the recorded images to the image synthesis unit 26 as appropriate.

The image output unit 28 outputs the synthetic eye fundus image supplied from the image synthesis unit 26 to the external. For example, the image output unit 28 supplies the synthetic eye fundus image to an external display and displays the synthetic eye fundus image on the display.

<Explanation of Image Generation Processing>

Next, the operation of the eye fundus image photographing device 11 illustrated in FIG. 2 is described.

When an operation by a doctor or the like who conducts an eye fundus examination or the like of a subject is received and an eye fundus image is instructed to be photographed, the eye fundus image photographing device 11 starts image generation processing that is processing to photograph the eye fundus of eye EY11 that is an object and output a synthetic eye fundus image. Hereafter, the image generation processing by the eye fundus image photographing device 11 is described with reference to the flowchart in FIG. 3.

Figure 3:
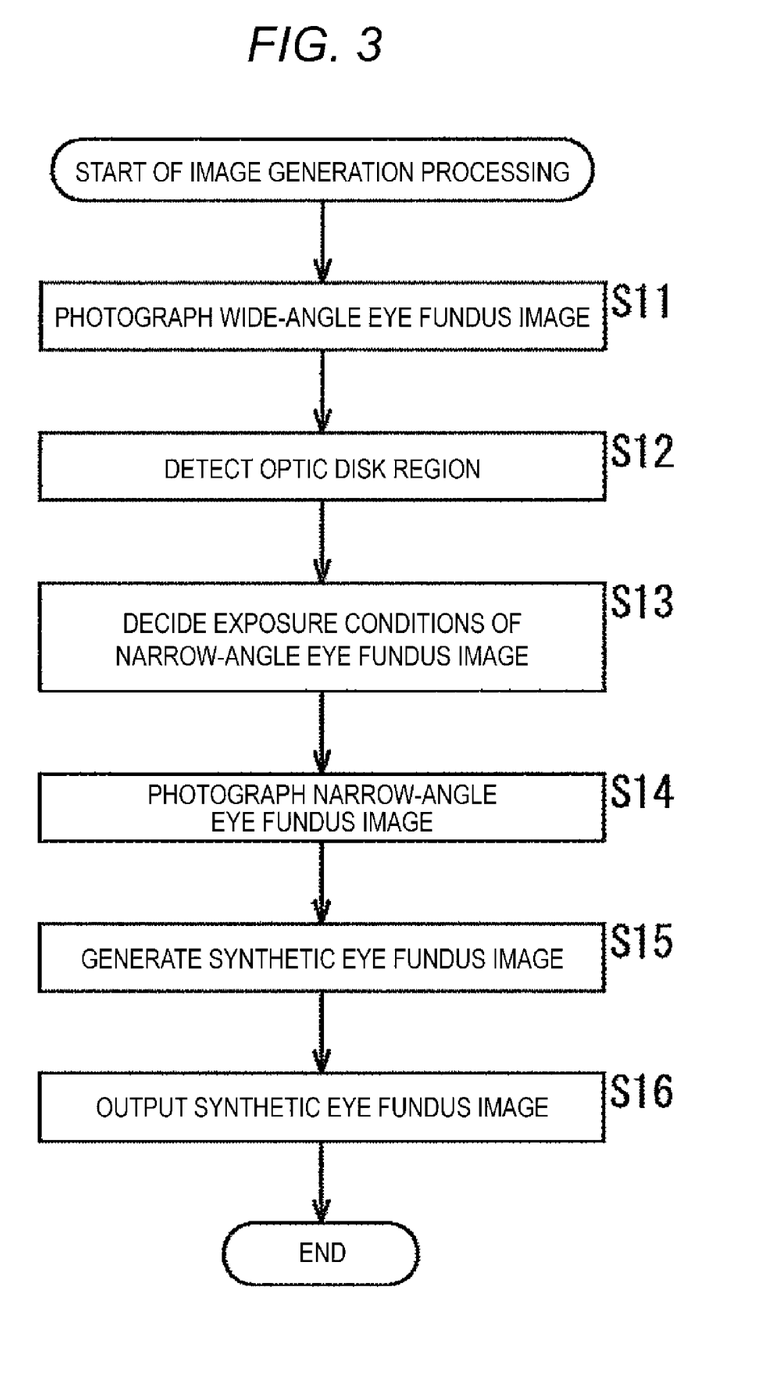
FIG. 3 is a flowchart to describe image generation processing.

In step S11, the image sensor 23 photographs a wide-angle eye fundus image.

For example, exposure conditions at the time of photographing of the wide-angle eye fundus image are defined by an input operation for the eye fundus image photographing device 11 by the user such as a doctor or by exposure control using infrared light by the eye fundus image photographing device 11. The control unit 25 controls the exposure time in the image sensor 23 and the light quantity of illumination light from the light source 21 such that photographing is performed on the defined exposure conditions.

Here, the exposure conditions at the time of the photographing of the wide-angle eye fundus image are set to exposure conditions on which a peripheral area excluding the optic disk region in the eye fundus is not saturated as described above and the peripheral area can be sufficiently observed. Although exposure conditions in an eye fundus camera in the related art are set to conditions on which blown-out highlights are not caused as much as possible in optic disk region V11, the exposure conditions in the photographing in step S11 are set to conditions on which it is brighter than the related art in order to acquire an image of higher quality in the peripheral area. Moreover, at the time of the photographing of the wide-angle eye fundus image, the photographing is performed using all effective pixels provided on the light receiving surface of the image sensor 23.

The light source 21 emits illumination light according to the control of the control unit 25 and irradiates the illumination light to an eye fundus area that is an object through the optical system 22. Moreover, the optical system 22 focuses light entered from the eye fundus area and forms it on the light receiving surface of the image sensor 23.

The image sensor 23 photographs the wide-angle eye fundus image by performing photoelectric conversion of the light entered from the optical system 22 according to the control of the control unit 25 and supplies it to the optic disk detection unit 24 and the image synthesis unit 26. That is, the image sensor 23 outputs a signal including pixel signals output from the all effective pixels provided on the light receiving surface, as an image signal of the wide-angle eye fundus image.

By this means, for example, wide-angle eye fundus image WP11 illustrated in FIG. 1 is acquired. The wide-angle eye fundus image is assumed to be a still image of many pixels in which the macular region or the optic disk region appears as the object.

Further, the image synthesis unit 26 supplies the wide-angle eye fundus image supplied from the image sensor 23 to the frame memory 27 to temporarily record it.

Thus, if the wide-angle eye fundus image is photographed on appropriate exposure conditions with respect to the peripheral area excluding the optic disk region such as the macular region of the eye fundus area, it is possible to acquire an image in which it is possible to sufficiently diagnose the peripheral area such as the macular region of low reflectivity, as the wide-angle eye fundus image. In such photographing under high illumination intensity, although the area of the optic disk region with high reflectivity on the wide-angle eye fundus image is saturated and blown-out highlights are caused, it is possible to acquire an image of high quality with less noise as an image of the peripheral area.

In step S12, the optic disk detection unit 24 detects the optic disk region from the wide-angle eye fundus image supplied from the image sensor 23, on the basis of the brightness value of each pixel of the wide-angle eye fundus image and the composition of the wide-angle eye fundus image.

For example, in a case where an eye fundus image is photographed, as illustrated in FIG. 1, the composition is often assumed to be a composition in which optic disk region V11 is positioned in an area on the slightly right side of the center of wide-angle eye fundus image WP11 and macular region V12 is positioned in an area on the slightly left side of the center of wide-angle eye fundus image WP11. Moreover, since the optic disk region has higher reflectivity than the peripheral area as described above, the area of the optic disk region on the wide-angle eye fundus image is supposed to have higher brightness than the peripheral area.

Therefore, for example, by assuming that the optic disk region exists in the area on the slightly right side of the center of the wide-angle eye fundus image, the optic disk detection unit 24 assumes an area as the optic disk region, where the area is in the area on the slightly right side of the center of the wide-angle eye fundus image and has a size equal to or greater than a specific area including pixels in which the brightness values are equal to or greater than a predetermined threshold. The optic disk detection unit 24 supplies the position of the area of the optic disk region on the wide-angle eye fundus image, which is acquired as a result of the detection, and the wide-angle eye fundus image to the control unit 25.

In step S13, the control unit 25 decides exposure conditions of a narrow-angle eye fundus image, on the basis of the position of the area of the optic disk region and the wide-angle eye fundus image which are supplied from the optic disk detection unit 24.

For example, in a case where pixel signals are read out every line including pixels arranged in the horizontal direction of the image sensor 23, the control unit 25 decides an area including the detected optic disk region on the wide-angle eye fundus image as the photographing range of the narrow-angle eye fundus image. Further, the control unit 25 controls the drive of the image sensor 23 such that the pixel signals are read out only from pixels configuring a line of the image sensor 23 corresponding to the decided photographing range area.

Thus, by reading out the pixel signals only from part of the lines configuring the light receiving surface of the image sensor 23, photographing at a high frame rate under low illumination intensity becomes possible. When the narrow-angle eye fundus image is photographed at a high frame rate, the influence of large motion of the eyeball can be suppressed and it is possible to acquire a narrow-angle eye fundus image of high quality without a blur.

Moreover, based on the brightness value of the peripheral area on the wide-angle eye fundus image, the control unit 25 decides exposure conditions on which pixels of the area of the optic disk region in the narrow-angle eye fundus image are not saturated and the optic disk region can be sufficiently observed, and controls the light source 21 and the image sensor 23 according to the exposure conditions. Actually, since the brightness of the area of the optic disk region is saturated in the wide-angle eye fundus image and is not possible to be measured, sufficiently dark exposure conditions on which blown-out highlights are not caused in the optic disk region may be set according to brightness value distribution of the peripheral area.

Specifically, the control unit 25 drives the image sensor 23 such that the narrow-angle eye fundus image is photographed at an exposure time (shutter speed) as the decided exposure condition, and controls the light source 21 such that the eye fundus is illuminated by the light quantity as the decided exposure condition.

When the exposure conditions of the narrow-angle eye fundus image are defined using the wide-angle eye fundus image, it is possible to photograph the narrow-angle eye fundus image on optimal exposure conditions without user's operation. By this means, it is possible to prevent blown-out highlights (saturation) in the optic disk region that is an object of the narrow-angle eye fundus image, and suppress noise in the peripheral area. Moreover, since photographing does not have to be performed in order to only acquire information defining exposure conditions, it is possible to promptly acquire a requested eye fundus image by a smaller number of photographing.

In step S14, the image sensor 23 photographs the narrow-angle eye fundus image at a high frame rate.

For example, according to the control of the control unit 25, the light source 21 emits illumination light by the light quantity defined as an exposure condition and irradiates the illumination light to an eye fundus area that is an object through the optical system 22. Moreover, the optical system 22 focuses light entered from the eye fundus area and forms it on the light receiving surface of the image sensor 23.

The image sensor 23 photographs the narrow-angle eye fundus image by performing photoelectric conversion of the light entered from the optical system 22 at the exposure time defined as an exposure condition, according to the control of the control unit 25, and supplies it to the image synthesis unit 26. That is, the image sensor 23 outputs signals including pixel signals output from pixels configuring lines within a range defined as the photographing range of the narrow-angle eye fundus image among all lines set on the light receiving surface, as an image signal of the narrow-angle eye fundus image.

By this means, for example, narrow-angle eye fundus image NP11 illustrated in FIG. 1 is acquired. The narrow-angle eye fundus image is assumed to be each frame of a moving image in which an area near the optic disk region appears as an object, or continuously photographed still images.

Further, the image synthesis unit 26 supplies the narrow-angle eye fundus image supplied from the image sensor 23 to the frame memory 27 to temporarily record it.

Thus, when the narrow-angle eye fundus image is photographed on appropriate exposure conditions with respect to the area of the optic disk region in the eye fundus area, it is possible to acquire an image in which it is possible to sufficiently diagnose the area of the optic disk region with high reflectivity, as the narrow-angle eye fundus image.

Here, an example has been described where the identical light source is used as the light source 21 for illumination of an object at the time of photographing of the wide-angle eye fundus image and the light source 21 for illumination of an object at the time of photographing of the narrow-angle eye fundus image. In a case where the identical light source 21 is used in this way, since the color temperature of illumination light is identical between at the time of the photographing of the wide-angle eye fundus image and at the time of the photographing of the narrow-angle eye fundus image, it is possible to suppress that the tone of a synthetic eye fundus image changes, and it is possible to acquire an image of high quality. However, different light sources may be used between at the time of the photographing of the wide-angle eye fundus image and at the time of the photographing of the narrow-angle eye fundus image.

In step S15, the image synthesis unit 26 synthesizes the wide-angle eye fundus image and the narrow-angle eye fundus image, which are recorded in the frame memory 27, and generates the synthetic eye fundus image.

For example, the image synthesis unit 26 performs gain adjustment on the narrow-angle eye fundus image such that the difference in illumination intensity between the narrow-angle eye fundus image and the wide-angle eye fundus image is compensated, and performs image conversion such that the brightness is matched between the narrow-angle eye fundus image and the wide-angle eye fundus image. At this time, since the brightness values of pixels of the optic disk region are saturated when the narrow-angle eye fundus image is amplified by the gain adjustment, the image synthesis unit 26 has to record the narrow-angle eye fundus image subjected to the gain adjustment in a buffer with a sufficiently large width. Next, the image synthesis unit 26 detects the motion between the narrow-angle eye fundus image and the wide-angle eye fundus image. Further, by performing motion compensation on the narrow-angle eye fundus image according to the motion detection result, the image synthesis unit 26 shifts the narrow-angle eye fundus image such that the area of the optic disk region on the wide-angle eye fundus image and the area of the optic disk region on the narrow-angle eye fundus image are overlapped, and, after compensating the motion of the eyeball of the subject, synthesizes the narrow-angle eye fundus image with the wide-angle eye fundus image.

For example, in the gain adjustment, it is calculated what times the wide-angle eye fundus image to be photographed is as bright as the narrow-angle eye fundus image, from the ratio between the exposure conditions at the time of photographing of the narrow-angle eye fundus image and the exposure conditions at the time of photographing of the wide-angle eye fundus image, and the gain of the narrow-angle eye fundus image is adjusted on the basis of this ratio. Here, in addition, the brightness value average of peripheral pixels of the optic disk region in the narrow-angle eye fundus image and the brightness value average in an area corresponding to the peripheral pixels in the narrow-angle eye fundus image near the optic disk region in the wide-angle eye fundus image may be calculated, and the gain may be subjected to fine adjustment such that these brightness value averages are matched.

Moreover, for example, the synthesis of the narrow-angle eye fundus image with the wide-angle eye fundus image is performed by weighting addition of the image such as alpha blending processing. In such a case, the pixel values of the narrow-angle eye fundus image and wide-angle eye fundus image are added according to the weight based on the brightness value of each area, for example, the weight of the narrow-angle eye fundus image, that is, the contribution rate to a synthetic eye fundus image is increased in the area of the optic disk region, and the weight of the wide-angle eye fundus image is increased in an area different from the optic disk region.

Thus, one synthetic eye fundus image is acquired by synthesizing each narrow-angle eye fundus image with the wide-angle eye fundus image while performing motion compensation and illumination intensity compensation. Here, since the synthetic eye fundus image is a high dynamic range image, the bit width is large. The image synthesis unit 26 converts the synthetic eye fundus image of the large bit width into a bit width corresponding to a standard image signal. At this time, processing such as gradation correction may be performed on the synthetic eye fungus image or an arbitrary brightness range may be cut out from the image of the large bit width by parameters given from an external input device such as a keyboard and a setting button which are not illustrated. The image synthesis unit 26 supplies the acquired synthetic eye fundus image to the image output unit 28.

By photographing multiple narrow-angle eye fundus images at a high frame rate under low illumination intensity in this way, performing motion compensation on each acquired narrow-angle eye fundus image and synthesizing the result with a wide-angle eye fundus image, it is possible to acquire a synthetic eye fundus image with high resolution by the super-resolution effect.

Generally, it is known that, when multiple images with different sampling positions are synthesized, high resolution of images is realized. In other words, it is known that, when multiple images which are acquired by photographing the same object and photographed in mutually different sampling positions are synthesized, an image with high resolution can be acquired as a super-resolution effect. In a case where the eyeball of the subject moves at the time of photographing of narrow-angle eye fundus images, since the narrow-angle eye fundus images with different photographing times are photographed in mutually different sampling positions respectively, when motion compensation is performed on these narrow-angle eye fundus images to synthesize them with a wide-angle eye fundus image, it is possible to acquire a synthetic eye fundus image with high resolution by the super-resolution effect.

Moreover, by synthesizing the wide-angle eye fundus image photographed under high illumination intensity and the narrow-angle eye fundus image photographed under low illumination intensity to produce a synthetic eye fundus image, it is possible to acquire an image of a high dynamic range in which it is possible to sufficiently observe each region of the eye fundus.

In step S16, the image output unit 28 outputs the synthetic eye fundus image supplied from the image synthesis unit 26 to the external, and the image generation processing terminates. The synthetic eye fundus image output from the image output unit 28 is supplied to, for example, a display and displayed.

As described above, after photographing a wide-angle eye fundus image on appropriate exposure conditions with respect to a peripheral area, the eye fundus image photographing device 11 photographs a narrow-angle eye fundus image on appropriate exposure conditions with respect to the area of an optic disk region, which is defined on the basis of the wide-angle eye fundus image, and synthesizes the wide-angle eye fundus image and the narrow-angle eye fundus image.

Thus, by synthesizing multiple images photographed on exposure conditions appropriate in areas with different reflectivities, it is possible to acquire a synthetic eye fundus image of high quality. Moreover, by performing motion compensation on multiple narrow-angle eye fundus images and synthesizing each of the narrow-angle eye fundus images acquired as a result with a wide-angle eye fundus image, it is possible to acquire a synthetic eye fundus image of higher quality by the super-resolution effect.

Moreover, although miosis is caused when strong light is irradiated to subject's eyes as illumination light at the time of non-mydriatic photographing, wide-angle photographing, that is, a wide-angle eye fundus image is photographed in only the first photographing in the eye fundus image photographing device 11, and, in subsequent photographing, a narrow-angle eye fundus image in which the photographing range is narrower and which is less subject to the influence of the miosis is photographed. Therefore, according to the eye fundus image photographing device 11, it is possible to acquire a synthetic eye fundus image of high quality even at the time of non-mydriatic photographing.

Here, although an example has been described above where motion compensation with respect to a narrow-angle eye fundus image is performed, the photographing range of the image sensor 23 may be corrected on the basis of the photographed narrow-angle eye fundus image. In such a case, the optic disk detection unit 24 detects an optic disk region from the photographed narrow-angle eye fundus image, the control unit 25 defines the photographing range of the narrow-angle eye fundus image on the basis of the detection result and controls the image sensor 23 such that pixel signals are read out from lines within the photographing range. Further, the image sensor 23 photographs the next narrow-angle eye fundus image according to the control of the control unit 25.

By the way, the series of processing described above can be performed by hardware and can be performed by software. In a case where the series of processing is performed by software, a program configuring the software is installed in a computer. Here, the computer includes a computer incorporated in dedicated hardware and, for example, a general-purpose computer that can execute various functions by installing various programs.

Figure 4:
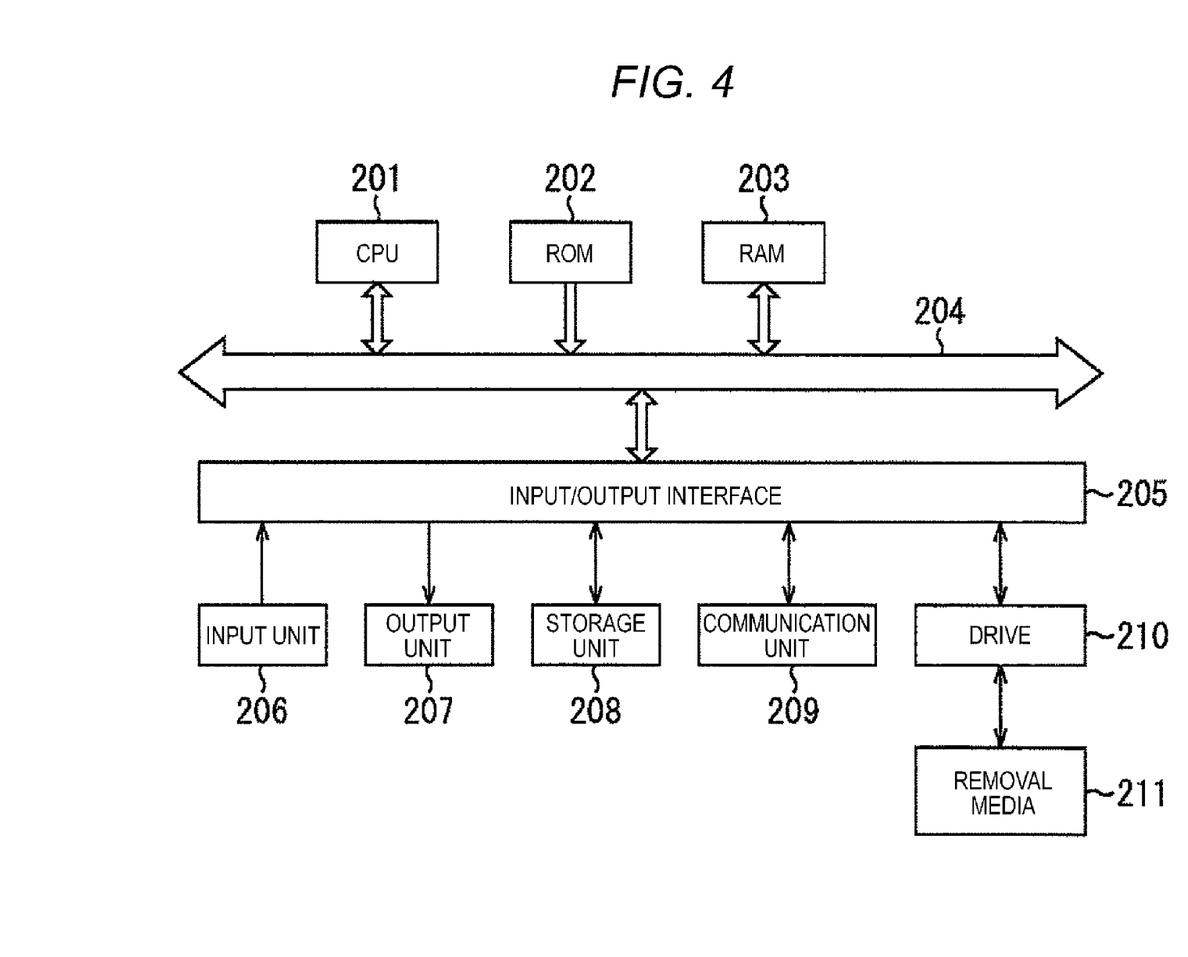
FIG. 4 is a diagram illustrating a configuration example of a computer.

FIG. 4 is a block diagram illustrating a configuration example of hardware of a computer that performs the above-mentioned series of processing by a program.

A CPU 201, a ROM 202 and a RAM 203 are mutually connected by a bus 204 in the computer.

Furthermore, an input/output interface 205 is connected with the bus 204. An input unit 206, an output unit 207, a recording unit 208, a communication unit 209 and a drive 210 are connected with the input/output interface 205.

The input unit 206 includes a keyboard, a mouse, a microphone and an image sensor, and the like. The output unit 207 includes a display, a speaker and a light source, and the like. The recording unit 208 includes a hard disk and a nonvolatile memory, and the like. The communication unit 209 includes a network interface, and the like. The drive 210 drives removable media 211 such as a magnetic disk, an optical disk, a magnet-optical disk and a semiconductor memory.

In the computer configured as above, for example, when the CPU 201 executes a program recorded in the recording unit 208 by loading it on the RAM 203 through the input/output interface 205 and the bus 204, the above-mentioned series of processing is performed.

For example, the program executed by the computer (CPU 201) can be recorded in the removable media 211 as package media or the like and provided. Moreover, it is possible to provide the program through a wire or wireless transmission medium such as a local area network, the Internet and digital satellite broadcasting.

In the computer, the program can be installed in the recording unit 208 through the input/output interface 205 by attaching the removable media 211 to the drive 210. Moreover, the program can be received in the communication unit 209 through a wire or wireless transmission medium and installed in the recording unit 208. Additionally, the program can be installed in the ROM 202 or the recording unit 208 beforehand.

Here, the program executed by the computer may be a program in which processing is performed in time series along the order described in the present specification, or may be a program in which processing is performed according at requested timing such as the time when calling is performed.

Moreover, embodiments of the present technology are not limited to the above-mentioned embodiments, and various changes can be made without departing from the scope of the present technology.

For example, the present technology can adopt a configuration of cloud computing that processes one function in a distributed and cooperative manner through a network.

Moreover, each step described in the above-mentioned flowchart can be executed by one device or executed by multiple devices in a distributed manner.

In addition, in a case where multiple items of processing are included in one step, the multiple items of processing included in one step can be performed by one device or performed by multiple devices in a distributed manner.

In addition, the present technology can adopt the following configuration.

(1)

An image processing device comprising:

a detection unit configured to detect a narrow-angle area of a wide-angle image, wherein the wide-angle image was generated using a first exposure condition, the first exposure condition based on a first area of the wide-angle image, different from the narrow-angle area;

a control unit configured to determine a second exposure condition for the narrow-angle area; and an image synthesis unit configured to generate a synthetic image by synthesizing a narrow-angle image and the wide-angle image, wherein the narrow-angle image has a narrower angle of view than the wide-angle image and was generated using the second exposure condition.

(2)

The image processing device according to (1), wherein the image synthesis unit generates the synthesis image by synthesizing a plurality of narrow-angle images that are continuously photographed and the wide-angle image.

(3)

The image processing device according to (2), wherein the image synthesis unit performs motion compensation on the plurality of narrow-angle images and synthesizes the plurality of narrow-angle images acquired by the motion compensation and the wide-angle image.

(4)

The image processing device according to (2), wherein the control unit determines a pixel area in order to photograph the narrow-angle image using the pixel area and based on a detection of the narrow-angle area.

(5)

The image processing device according to (2), wherein the control unit controls a light source that outputs illumination light irradiated to the narrow-angle area or a photographing unit that photographs the narrow-angle image based on the second exposure condition with respect to the narrow-angle area.

(6)

The image processing device according to (1), wherein the control unit controls a light source such that the narrow-angle area is illuminated by equal light outputs from the light source when the wide-angle image is photographed and when the narrow-angle image is photographed.

(7)

The image processing device according to (1), wherein the second exposure condition is set such that a pixel of the narrow-angle area in the narrow-angle image is not saturated.

(8)

An eye fundus image processing device comprising:

a detection unit configured to detect a narrow-angle area of an eye fundus from a wide-angle image, wherein the wide-angle image was generated using a first exposure condition, the first exposure condition based on a first area of the eye fundus, different from the narrow-angle area;

a control unit configured to determine a second exposure condition for the narrow-angle area of the eye fundus; and an image synthesis unit configured to generate a synthetic image by synthesizing a narrow-angle image and the wide-angle image, wherein the narrow-angle image has a narrower angle of view than the wide-angle image and was generated for the narrow-angle area of the eye fundus using the second exposure condition.

(9)

The eye fundus image processing device according to (8), wherein the narrow-angle area of the eye fundus is an area of an optic disk.

(10)

An image processing method comprising:

detecting a narrow-angle area of a wide-angle image, wherein the wide-angle image was generated using a first exposure condition, the first exposure condition based on a first area of the wide-angle image, different from the narrow-angle area;

determining a second exposure condition for the narrow-angle area; and generating a synthetic image by synthesizing a narrow-angle image and the wide-angle image, wherein the narrow-angle image has a narrower angle of view than the wide-angle image and was generated for the narrow-angle area using the second exposure condition.

(11)

An image photographing method comprising:

photographing a wide-angle image using a first exposure condition based on a first area of the wide-angle image;

determining a second exposure condition for a narrow-angle area, different from the first area, based on the wide-angle image; and photographing a narrow-angle image having a narrower angle of view than the wide-angle image, based on the second exposure condition and the narrow-angle area.

(12)

The image photographing method according to (11), wherein the narrow-angle area is detected based on the wide-angle image, and the second exposure condition with respect to the narrow-angle area is determined based on a detection result of the narrow-angle area.

(13)

The image photographing method according to (11), wherein photographing a narrow-angle image comprises continuously photographing a plurality of narrow-angle images.

(14)

The image photographing method according to (12), wherein the narrow-angle image is photographed using a pixel area of a photographing unit, the pixel area determined based on the detection result of the narrow-angle area.

(15)

The image photographing method according to (11), wherein a light source is controlled such that the narrow-angle area is illuminated by equal light outputs from the light source when photographing the wide-angle image and when photographing the narrow-angle image.

(16)

The image photographing method according to (11), wherein the second exposure condition is set such that a pixel of the narrow-angle area in the narrow-angle image is not saturated.

(17)

An eye fundus image photographing method comprising:

photographing a wide-angle image using a first exposure condition based on a first area of the wide-angle image;

determining a second exposure condition for a narrow-angle area of an eye fundus, different from the first area, based on the wide-angle image; and photographing a narrow-angle image having a narrower angle of view than the wide-angle image, based on the second exposure condition and the narrow-angle area of the eye fundus.

(18)

The eye fundus image photographing method according to (17), wherein the narrow-angle area of the eye fundus is an area of an optic disk.

(19)

An eye fundus image photographing device comprising:

a photographing unit configured to photograph a wide-angle image using a first exposure condition based on a first area of an eye fundus, and photograph a narrow-angle image, having a narrower angle of view than the wide-angle image, using a second exposure condition based on a narrow-angle area of the eye fundus;

a detection unit configured to detect the narrow-angle area of the eye fundus from the wide-angle image based on the wide-angle image;

a control unit configured to determine the second exposure condition with respect to the narrow-angle area of the eye fundus based on the detection of the narrow-angle area of the eye fundus; and an image synthesis unit configured to generate a synthetic image by synthesizing the narrow-angle image and the wide-angle image.

(20)

An image processing device including:

a detection unit configured to detect a specific area from a wide-angle image based on the wide-angle image photographed on an appropriate exposure condition with respect to a different area from the specific area;

a control unit configured to decide an appropriate exposure condition with respect to the specific area based on a detection result of the specific area; and an image synthesis unit configured to generate a synthetic image by synthesizing a narrow-angle image with a narrower angle of view than the wide-angle image, and the wide-angle image, where the narrow-angle image assumes the specific area as an object and is photographed on the appropriate exposure condition with respect to the specific area.

(21)

The image processing device according to (20), wherein the image synthesis unit generates the synthesis image by synthesizing a plurality of the narrow-angle images that is continuously photographed and the wide-angle image.

(22)

The image processing device according to (21), wherein the image synthesis unit performs motion compensation on the plurality of the narrow-angle images and synthesizes the narrow-angle images acquired by the motion compensation and the wide-angle image.

(23)

The image processing device according to (21) or (22), wherein the control unit decides an area used to photograph the narrow-angle image in a pixel area of a photographing unit that photographs the narrow-angle image, based on the detection result of the specific area.

(24)

The image processing device according to any one of (20) to (23), wherein the control unit controls a light source that outputs illumination light irradiated to the object or a photographing unit that photographs the narrow-angle image based on the appropriate exposure condition with respect to the specific area.

(25)

The image processing device according to any one of (20) to (24), wherein the control unit controls the light source such that the object is illuminated by illumination light output from the identical light source when the wide-angle image is photographed and the narrow-angle image is photographed.

(26)

The image processing device according to any one of (20) to (25), wherein the appropriate exposure condition with respect to the specific area is set to a condition on which a pixel of the specific area in the narrow-angle image is not saturated.

(27)

An eye fundus image processing device including:

a detection unit configured to detect a specific area of an eye fundus from a wide-angle image based on the wide-angle image photographed on an appropriate exposure condition with respect to a different area from the specific area of the eye fundus; a control unit configured to decide an appropriate exposure condition with respect to the specific area of the eye fundus based on a detection result of the specific area of the eye fundus; and an image synthesis unit configured to generate a synthetic image by synthesizing a narrow-angle image of a narrower angle of view than the wide-angle image, and the wide-angle image, where the narrow-angle image assumes the specific area of the eye fundus as an object and is photographed on the appropriate exposure condition with respect to the specific area of the eye fundus.

(28)

The eye fundus image processing device according to (27), wherein the specific area of the eye fundus is set to an area of an optic disk.

(29)

An image processing method including:

detecting a specific area from a wide-angle image based on the wide-angle image photographed on an appropriate exposure condition with respect to a different area from the specific area;

deciding an appropriate exposure condition with respect to the specific area based on a detection result of the specific area; and generating a synthetic image by synthesizing a narrow-angle image with a narrower angle of view than the wide-angle image, and the wide-angle image, where the narrow-angle image assumes the specific area as an object and is photographed on the appropriate exposure condition with respect to the specific area.

(30)

An image photographing method including:

performing first photographing to photograph a wide-angle image on an appropriate exposure condition with respect to a different area from a specific area;

deciding an appropriate exposure condition with respect to the specific area based on the wide-angle image; and performing second photographing to photograph a narrow-angle image, which assumes the specific area as an object and has a narrower angle of view than the wide-angle image, on the appropriate exposure condition with respect to the specific area.

(31)

The image photographing method according to (30), wherein the specific area is detected from the wide-angle image based on the wide-angle image, and the appropriate exposure condition with respect to the specific area is decided based on a detection result of the specific area.

(32)

The image photographing method according to (30) or (31), wherein a plurality of the narrow-angle images is continuously photographed in the second photographing.

(33)

The image photographing method according to (31), wherein, in the second photographing, the narrow-angle image is photographed using an area of a predetermined range in a pixel area of a photographing unit, which is decided based on the detection result of the specific area.

(34)

The image photographing method according to any one of (30) to (33), wherein, in the first photographing and the second photographing, the light source is controlled such that the object is illuminated by illumination light output from the identical light source.

(35)

The image photographing method according to any one of (30) to (34), wherein the appropriate exposure condition with respect to the specific area is set to a condition on which a pixel of the specific area in the narrow-angle image is not saturated.

(36)

An eye fundus image photographing method including:

performing first photographing to photograph a wide-angle image on an appropriate exposure condition with respect to a different area from a specific area of an eye fundus;

deciding an appropriate exposure condition with respect to the specific area of the eye fundus based on the wide-angle image; and performing second photographing to photograph a narrow-angle image, which assumes the specific area of the eye fundus as an object and has a narrower angle of view than the wide-angle image, on the appropriate exposure condition with respect to the specific area of the eye fundus.

(37)

The eye fundus image photographing method according to (36), wherein the specific area of the eye fundus is set to an area of an optic disk.

(38)

An eye fundus image photographing device including:

a photographing unit configured to photograph a wide-angle image on an appropriate exposure condition with respect to a different area from a specific area of an eye fundus and photograph a narrow-angle image, which assumes the specific area of the eye fundus as an object and has a narrower angle of view than the wide-angle image, on an appropriate exposure condition with respect to the specific area of the eye fundus;

a detection unit configured to detect the specific area of the eye fundus from the wide-angle image based on the wide-angle image;

a control unit configured to decide the appropriate exposure condition with respect to the specific area of the eye fundus based on a detection result of the specific area of the eye fundus; and an image synthesis unit configured to generate a synthetic image by synthesizing the narrow-angle image and the wide-angle image.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

11 Eye fundus image photographing device
21 Light source
22 Optical system
23 Image sensor
24 Optic disk detection unit
25 Control unit
26 Image synthesis unit

The invention claimed is:

1. An image processing device comprising:
   circuitry configured to
      detect a narrow-angle area of a wide-angle image, wherein the narrow-angle area is an area of an optic disc portion of an eye fundus, and the wide-angle image was generated using a first exposure condition, the first exposure condition based on a first area of the wide-angle image, different from the narrow-angle area;
      determine a second exposure condition for the narrow-angle area; and
      generate a synthetic image by synthesizing a narrow-angle image and the wide-angle image, wherein the narrow-angle image has narrower angle of view than the wide-angle image and was generated using the second exposure condition.

2. The image processing device according to claim 1, wherein the circuitry is configured to generate the synthesis image by synthesizing a plurality of narrow-angle images that are continuously photographed and the wide-angle image.

3. The image processing device according to claim 2, wherein the circuitry is configured to perform motion compensation on the plurality of narrow-angle images and synthesize the plurality of narrow-angle images acquired by the motion compensation and the wide-angle image.

4. The image processing device according to claim 2, wherein the circuitry is configured to determine a pixel area in order to photograph the narrow-angle image using the pixel area and based on a detection of the narrow-angle area.

5. The image processing device according to claim 1, wherein the circuitry is configured to control a light source that outputs illumination light irradiated to the narrow-angle area or a camera that photographs the narrow-angle image based on the second exposure condition with respect to the narrow-angle area.

6. The image processing device according to claim 1, wherein the circuitry is configured to control a light source such that the narrow-angle area is illuminated by equal light outputs from the light source when the wide-angle image is photographed and when the narrow-angle image is photographed.

7. The image processing device according to claim 1, wherein the second exposure condition is set such that a pixel of the narrow-angle area in the narrow-angle image is not saturated.

8. An image processing method comprising:
   detecting a narrow-angle area of a wide-angle image, wherein the narrow-angle area is an area of an optic disc portion of an eye fundus, and the wide-angle image was generated using a first exposure condition, the first exposure condition based on a first area of the wide-angle image, different from the narrow-angle area;
   determining a second exposure condition for the narrow-angle area; and
   generating a synthetic image by synthesizing a narrow-angle image and the wide-angle image, wherein
   the narrow-angle image has a narrower angle of view than the wide-angle image and was generated for the narrow-angle area using the second exposure condition.

9. An image photographing method comprising:
   photographing a wide-angle image using a first exposure condition based on a first area of the wide-angle image;
   determining a second exposure condition for a narrow-angle area, different from the first area, based on the wide-angle image, wherein the narrow-angle area is an area of an optic disc portion of an eye fundus; and
   photographing a narrow-angle image having a narrower angle of view than the wide-angle image, based on the second exposure condition and the narrow-angle area.

10. The image photographing method according to claim 9, wherein:
   the narrow-angle area is detected based on the wide-angle image; and the second exposure condition with respect to the narrow-angle area is determined based on a detection result of the narrow-angle area.

11. The image photographing method according to claim 10, wherein, the narrow-angle image is photographed using a pixel area of a camera, the pixel area determined based on the detection result of the narrow-angle area.

12. The image photographing method according to claim 9, wherein photographing the narrow-angle image comprises continuously photographing a plurality of narrow-angle images.

13. The image photographing method according to claim 9, wherein a light source is controlled such that the narrow-angle area is illuminated by equal light outputs from the light source when photographing the wide-angle image and when photographing the narrow-angle image.

14. The image photographing method according to claim 9, wherein the second exposure condition is set such that a pixel of the narrow-angle area in the narrow-angle image is not saturated.

15. An eye fundus image photographing device comprising:
    a camera configured to photograph a wide-angle image using a first exposure condition based on a first area of an eye fundus, and photograph a narrow-angle image, having a narrower angle of view than the wide-angle image, using a second exposure condition based on a narrow-angle area of the eye fundus, wherein the narrow-angle area of the eye fundus is an area of an optic disc portion of the eye fundus; and
    circuitry configured to
        detect the narrow-angle area of the eye fundus from the wide-angle image based on the wide-angle image;
        determine the second exposure condition with respect to the narrow-angle area of the eye fundus based on the detection of the narrow-angle area of the eye fundus; and
        generate a synthetic image by synthesizing the narrow-angle image and the wide-angle image.

* * * * *